(12) United States Patent  
Hunter

(10) Patent No.: US 7,620,289 B2  
(45) Date of Patent: Nov. 17, 2009

(54) SPRING-LOADED FIBER COUPLER COVER WITH CAM PROFILE

(75) Inventor: Lowell D. Hunter, Los Gatos, CA (US)

(73) Assignee: AMS Research Corporation, Minnetonka, MN (US)

( * ) Notice: Subject to any disclaimer, the term of this patent is extended or adjusted under 35 U.S.C. 154(b) by 0 days.

(21) Appl. No.: 12/152,366

(22) Filed: May 14, 2008

(65) Prior Publication Data

US 2008/0285935 A1 Nov. 20, 2008

Related U.S. Application Data

(60) Provisional application No. 60/917,793, filed on May 14, 2007.

(51) Int. Cl.
*G02B 6/00* (2006.01)
*A61N 5/06* (2006.01)

(52) U.S. Cl. .......................................... 385/139; 607/89

(58) Field of Classification Search ................. 385/139; 607/89

See application file for complete search history.

(56) References Cited

U.S. PATENT DOCUMENTS

| 5,506,922 | A | * | 4/1996 | Grois et al. | .................... 385/75 |
| 5,708,745 | A | * | 1/1998 | Yamaji et al. | ................. 385/92 |
| 5,883,995 | A | * | 3/1999 | Lu | .............................. 385/75 |
| 7,283,718 | B2 | * | 10/2007 | Zaina et al. | ................. 385/139 |

* cited by examiner

*Primary Examiner*—Charlie Peng
(74) *Attorney, Agent, or Firm*—Jose' W. Jimenez; Kimberly K. Baxter; Gregory L. Koeller

(57) ABSTRACT

A medical laser unit having a spring-loaded coupler cover for protecting a fiber optic coupler from damage when an optical fiber is not coupled to the laser unit. When an optical fiber is attached to the fiber optic coupler, a cam arrangement on the spring-loaded coupler cover minimizes the force applied to the optical fiber by the spring-loaded coupler. The spring-loaded coupler cover includes a hinge assembly mounted above the fiber optic coupler such that the spring-loaded coupler is rotatably positionable between closed and open positions relative to the fiber optic coupler.

14 Claims, 4 Drawing Sheets

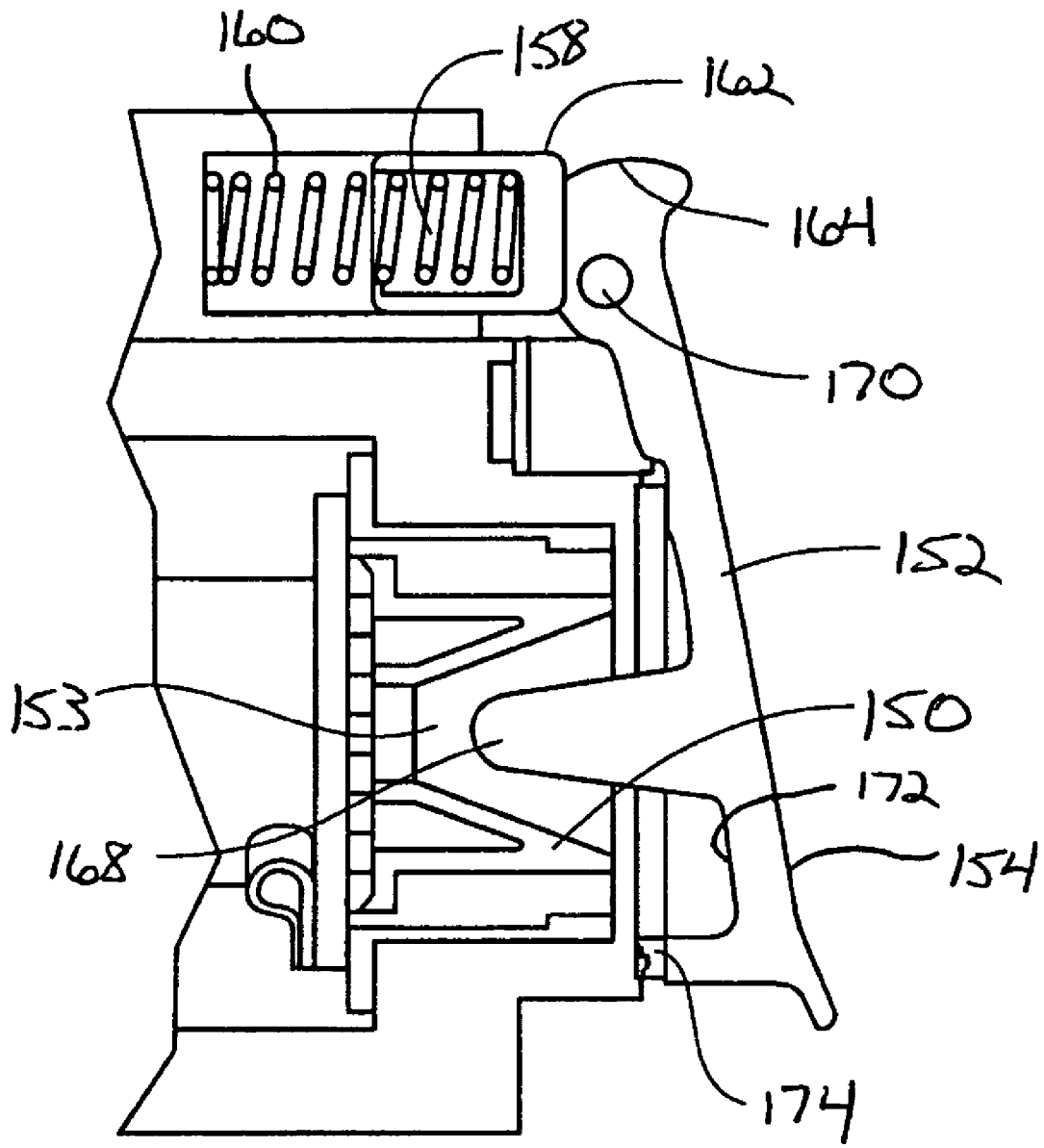
Fig. 3
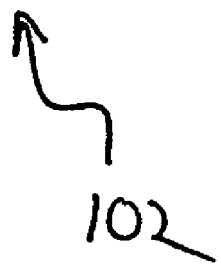

SPRING-LOADED FIBER COUPLER COVER WITH CAM PROFILE

CLAIM TO PRIORITY

The present utility patent application claims priority to U.S. Provisional Patent Application No. 60/917,793, filed May 14, 2007, and entitled "Spring-Loaded Fiber Coupler Cover with Cam Profile." The identified provisional patent application is hereby incorporated into the present specification in its entirety.

FIELD OF THE DISCLOSURE

This invention relates to the field of laser systems and fibers used for the treatment of soft tissue. More specifically, the present invention is directed to a laser system including a spring-loaded coupler cover for preventing dust from entering a fiber coupler at a laser output and damaging the fiber coupler when there is no optical fiber attached to the laser unit.

BACKGROUND OF THE INVENTION

Medical lasers have been used in treatment procedures in a variety of practice areas including, for example, urology, neurology, otorhinolaryngology, general anesthetic ophthalmology, dentistry, gastroenterology, cardiology, gynecology, and thoracic and orthopedic procedures. Generally, these procedures require precisely controlled delivery of energy. Due to the location of target tissue deep within the body, a medical procedure generally requires use of a flexible and maneuverable optical fiber. Depending upon the requirements for a light source, a variety of light sources can be used in conjunction with the optical fiber including, for example, pulsed lasers, diode lasers and neodymium lasers. Representative lasers used in medical treatment procedures include Ho:YAG lasers and Nd:YAG lasers.

Generally, in the treatment of body tissue with laser energy, a surgical probe is utilized. The surgical probe typically comprises an optical fiber coupled to a laser source wherein the probe can be positioned so that a probe tip can be positioned adjacent to the targeted tissue. Laser energy is directed out of the tip of the optical fiber onto desired portions of the targeted tissue. The laser optical fiber is coupled to the laser source through the fiber connector. When the laser optical fiber is not connected to the laser unit, generally a removable dust plug is used to cover the aperture in the fiber connector that is otherwise adapted to receive the proximate end of the optical fiber. When the optical fiber is connected to the laser unit through the fiber connector, the dust plug is removed and stored. Upon completion of the usage of the laser unit, the dust plug is replaced on the fiber connector. However, because the dust plug is removable, the plugs are often lost or users simply forget to re-install the dust plug after removing the optical fiber from the fiber connector.

Hence, there remains a need for a protective mechanism such that the fiber coupler does not remain open and exposed to dust when the optical fiber is not connected to the laser unit through the fiber coupler.

SUMMARY OF THE INVENTION

The present invention is directed to a medical laser unit having a spring-loaded coupler cover for protecting a fiber optic coupler from damage when an optical fiber is not coupled to the laser unit. The spring-loaded coupler cover is continually biased toward a closed position in which the spring loaded coupler cover prevents dust infiltration into the fiber optic coupler. The spring-loaded coupler cover can be manually adjusted to an open position when attaching an optical fiber to the fiber optic coupler. When an optical fiber is attached to the fiber optic coupler, a cam arrangement on the spring-loaded coupler cover minimizes the force applied to the optical fiber by the spring-loaded coupler. The spring-loaded coupler cover includes a hinge assembly mounted above the fiber optic coupler such that the spring-loaded coupler is rotatably positionable between closed and open positions relative to the fiber optic coupler. The spring-loaded coupler cover can include a guiding structure designed to enter an aperture on the fiber optic coupler such that the spring-loaded coupler cover is aligned and positioned over the fiber optic coupler in the closed position. The spring-loaded coupler cover can further include a dust seal that seals between the spring-loaded coupler cover and the fiber optic coupler in the closed position.

In another aspect, the present disclosure is directed to a method of protecting a laser unit, and more specifically a fiber optic coupler from damage to dust infiltration when an optical fiber is not attached to the laser unit. The method can include providing a laser unit having a spring-loaded coupler cover continually biased toward a closed position proximate a fiber optic coupler. The spring-loaded coupler cover can be manually adjusted to an open position to expose a laser output port within the fiber optic coupler. With the spring-loaded coupler cover in the open position, the optical fiber can be attached to the laser unit by coupling the optical fiber to the output port. With the optical fiber attached to the laser unit, the medical laser procedure can be performed wherein the laser unit delivers laser energy to tissue a tip on the optical fiber. Upon completion of the medical procedure, the optical fiber can be detached from the laser unit wherein the spring-loaded coupler cover is automatically biased to the closed position over the fiber optic coupler to prevent infiltration of dust into laser output port.

Although specific examples have been illustrated and described herein, it will be appreciated by those of ordinary skill in the art that any arrangement calculated to achieve the same purpose could be substituted for the specific examples shown. For example, other configurations could be substituted for the example fiber coupler cover noted above.

BRIEF DESCRIPTION OF THE DRAWINGS

These as well as other objects and advantages of this invention will be more completely understood and appreciated by referring to the following more detailed description of the presently preferred exemplary embodiments of the invention in conjunction with the accompanying drawings, of which:

FIG. 3 depicts a section view of the laser unit of FIG. 2 depicting the spring-loaded coupler cover in a closed position with respect to an optical fiber coupler.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives.

DETAILED DESCRIPTION OF EMBODIMENTS OF THE INVENTION

The present invention includes a laser unit having a spring-loaded coupler cover for protecting a fiber optic coupler from damage when an optical fiber is not coupled to the laser unit. The spring-loaded coupler cover prevents dust contamination that can result if a manual coupler cover is not attached to the fiber optic coupler upon removal of the optical fiber. When an optical fiber is attached to the fiber optic coupler, a cam arrangement on the spring-loaded coupler cover minimizes the force applied to the optical fiber by the spring-loaded coupler. The spring-loaded coupler cover includes a hinge assembly mounted above the fiber optic coupler such that the spring-loaded coupler is rotatably positionable between closed and open position relative to the fiber optic coupler. In one preferred embodiment, the spring-loaded coupler cover is attached to a Greenlight HPS system manufactured by American Medical Systems of Minnetonka, Minn. and as described in U.S. Pat. Nos. 6,554,824 and 6,986,764, which are herein incorporated by reference.

Figure 1:
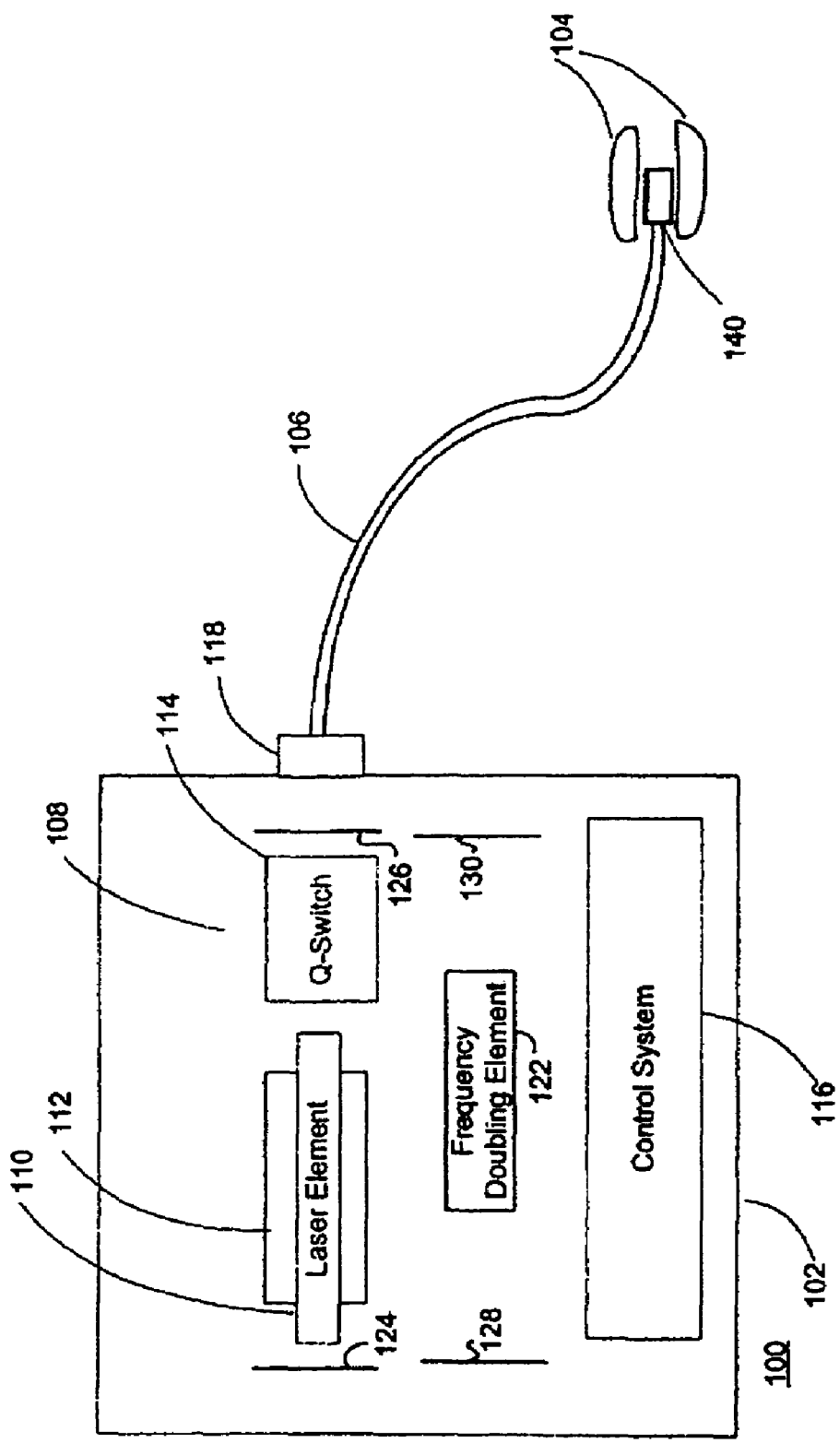
FIG. 1 depicts a schematic of a representative medical laser system with a fiber optic attached to the laser unit.

Referring to FIG. 1, there is depicted a block diagram showing an exemplary laser system 100 which may be employed for implementing the present invention. Laser system 100 includes a solid-state laser unit 102, which is used to generate laser light for delivery through optical fiber 106 to target tissue 104. Laser unit 102 is capable of being operated in a pulsed mode or continuous wave.

Laser unit 102 more specifically comprises a laser element assembly 110, pump source 112, and frequency doubling crystal 122. In the preferred-embodiment, laser element 110 outputs 1064 nm light which is focused into frequency doubling crystal 122 to create 532 nm light. According to one implementation, laser element assembly 110 may be neodymium doped YAG (Nd:YAG)crystal, which emits light having a wavelength of 1064 nm (infrared light) when excited by pump source 112. Laser element 110 may alternatively be fabricated from any suitable material wherein transition and lanthanide metal ions are disposed within a crystalline host (such as YAG, Lithium Yttrium Fluoride, Sapphire, Alexandrite, Spinel, Yttrium Orthoaluminate, Potassium Gadolinium Tungstate, Yttrium Orthovandate, or Lanthahum Scandium Borate). Laser element 110 is positioned proximal to pump source 112 and may be arranged in parallel relation therewith, although other geometries and configurations may be employed.

Pump source 112 may be any device or apparatus operable to excite laser element assembly 110. Non-limiting examples of devices which may be used as pump source 112, include: arc lamps, flashlamps, and laser diodes.

A Q-switch 114 disposed within laser unit 102 may be operated in a repetitive mode to cause a train of micropulses to be generated by laser unit 102. Typically the micropulses are less than 1 microsecond in duration separated by about 40 microseconds, creating a quasi-continuous wave train. Q-switch 114 is preferably of the acousto-optic type, but may alternatively comprise a mechanical device such as a rotating prism or aperture, an electro-optical device, or a saturable absorber.

Laser unit 102 is provided with a control system 116 for controlling and operating laser unit 102. Control system 116 will typically include a control processor which receives input from user controls (including but not limited to a beam on/off control, a beam power control, and a pulse duration control) and processes the input to accordingly generate output signals for adjusting characteristics of the output beam to match the user inputted values or conditions. With respect to pulse duration adjustment, control system 116 applies an output signal to a power supply (not shown) driving pump source 112 which modulates the energy supplied thereto, in turn controlling the pulse duration of the output beam.

Although FIG. 1 shows an internal frequency doubled laser, it is only by way of example. The infrared light can be internally or externally frequency doubled using non-linear crystals such as KTP, Lithium Triborate (LBO), or Beta Barium Borate (BBO) to produce 532 nm light. The frequency doubled, shorter wavelength light is better absorbed by the hemoglobin and char tissue, and promotes more efficient tissue ablation. Finally, the green light leaves only a thin char layer with little pre and post operative bleeding.

Laser unit 102 further includes an output port 118 couplable to optical fiber 106. Output port 118 directs the light generated by laser unit 102 into optical fiber 106 for delivery to tissue 104. Mirrors 124, 126, 128, and 130 direct light from the lasing element 110 to the frequency doubling crystal 122, in addition to forming the resonant cavity of the laser. Mirrors 124, 126, 128, and 130 are configured for focusing the light to form an image just in front of the frequency doubling crystal 122 on the side closer to mirror 130, and to compensate for thermal lensing in the lasing element. Although mirrors 124, 126, 128, and 130 are illustrated as flat and parallel to the walls of the laser, typically the focusing is achieved by curving and/or angling the mirrors. Alternatively transmissive optical elements could be used to focus the light and compensate for the thermal imaging. Mirrors 124, 128 and 130 reflect both the wavelength of light produced by the lasing element (e.g. 1064 nm) and the wavelength of the frequency doubled light (e.g. 532 nm). Mirror 126 only reflects the light originating from the lasing element 110 (e.g. 1064 nm) but is transparent to the frequency doubled light (e.g. 532 nm), forming an output window. Higher harmonic outputs may also be generated from the 1064 nm line, or other line amplified in the laser, including third and fourth harmonics, for shorter wavelengths. Other laser systems may be used, including but not limited to Sapphire lasers, diode lasers, and dye lasers, which are adapted to provide the output power and wavelengths described herein, including wavelengths in the ranges from 200 nm to 1000 nm and from 1100 nm to 1800 nm, for example.

While a bare fiber may be utilized for certain procedures, optical fiber 106 preferably terminates in a tip 140 having optical elements for shaping and/or orienting the beam emitted by optical fiber 106 so as to optimize the tissue ablation process, for example a side-firing fiber.

Figure 2:
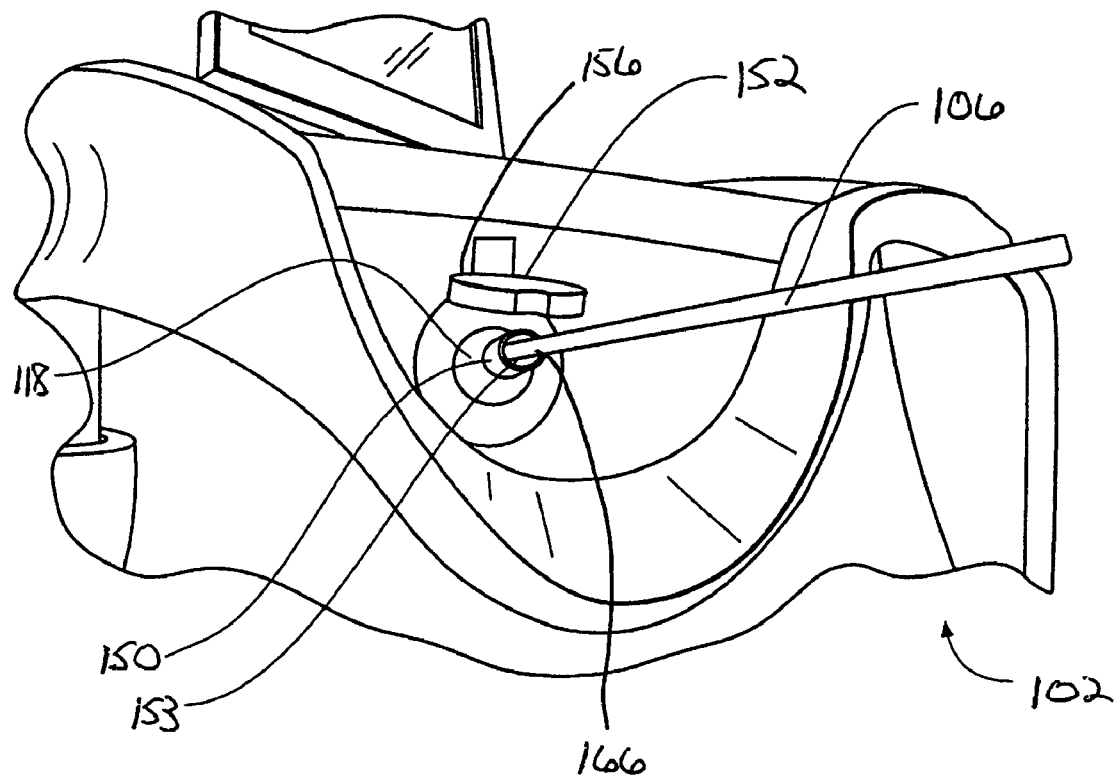
FIG. 2 depicts a laser unit having a spring-loaded coupler cover in an open position for accommodating attachment of an optical fiber according to an embodiment of the present invention.

The various lasers that are used for medical purposes, as noted above, generally include an optical fiber 106 through which the laser beam must pass. At times, the optical fiber 106 is in an extended, connected position, when the laser unit 102 is in use. The optical fiber 106 attaches to the laser unit 102 at a fiber optic coupler 150 at the output port 118 as shown in FIG. 2, whereby the tip 140 can be manipulated into position to accomplish a required task. When the optical fiber 106 is no longer needed, the optical fiber 106 is disconnected from the fiber optic coupler 150, and a spring-loaded coupler cover 152 is moved over an aperture 153 in the fiber optic coupler 150 through which the optical fiber 106 is connected to the laser unit 102. The spring-loaded coupler cover 152 covers the aperture 53 into which a proximate end of the optical fiber 106 was previously inserted. The spring-loaded coupler cover 152 prevents dust from entering the aperture 153 and possibly damaging optics located internally within the laser unit 102. More particularly, it is important that the aperture 153 be covered such that dust does damage optics with the fiber optic coupler 150.

The spring-loaded coupler cover 152 is biased toward a closed position 154 over the aperture 153 as shown in FIG. 3 to eliminate the possibility of having a non-covered fiber optic coupler 150 exposed to dust infiltration. The spring-loaded coupler cover 152 is manually shiftable from closed position 154 to an open position 156 as shown in FIG. 2 to allow the proximate end of optical fiber 106 to be inserted into aperture 153 and thus, optically connected to the output port 118 on the laser unit 102. Absent manual intervention, the spring-loaded coupler cover 152 assumes and is held in the closed position 154 under the influence of a biasing member 158. The biasing member 158 can take various forms, for example, a piston, a plunger, an extension scissor, or a spring 160. As shown in FIG. 3, spring 160 interfaces with a low friction cam follower 16. The low friction cam follower 162 is in communication with a cam profile 164 on the spring-loaded coupler cover 152. As the spring-loaded coupler cover 152 transitions between closed position 154 and open position 156, the low friction cam follower 162 rides on the cam profile 164. The interaction between the low friction cam follower 162 and the cam profile 164 prevents the spring-loaded coupler cover 152 from sticking or remaining in the open position 156 unless a manual force is intentionally applied.

When optical fiber 106 is connected to the laser unit 102, that is, the optical fiber 106 is operably coupled to the fiber optic coupler 150, the spring-loaded coupler cover 152 rests against a fiber connector 166. In this position, the spring 160, low friction cam follower 162 and the cam profile 164 minimize the amount of force applied to the fiber connector 166 and eliminate misalignment of the optical fiber 106 and the fiber optic coupler 150. The spring-loaded coupler cover 152 includes a positioning structure 168 that nestles in the aperture 153 of the fiber optic coupler 150, and assists in positioning and holding the spring-loaded coupler cover 152 in the closed position 154. Further, the positioning structure 168 at least partially blocks the aperture 153 to assist in keeping dust out of and away from optical components with the laser unit 102 and fiber optic coupler 150 specifically. The positioning structure 168 is shown in FIG. 3, however it will be understood that the positioning structure 168 is an optional component and can be omitted from the spring-loaded coupler cover 152 such that the spring-loaded coupler cover 152, absent additional blocking or covering structures, obstructs the aperture 153 in the fiber optic coupler 150.

The spring-loaded coupler cover 152, as noted in FIG. 2, includes a hinge assembly 170 above the fiber optic coupler 150 and the fiber connector 166. This configuration prevents dust from collecting on an inside surface 172 of the spring-loaded coupler cover 152 that is ultimately positioned adjacent to the fiber optic coupler 150 in the closed position 154. The spring-loaded coupler cover 152, optionally, includes at an unhinged or free end of the spring-loaded coupler cover 52 a dust seal 174, such as a foam dust seal, to further protect the fiber optic coupler 150 from dust and possible damage from dust, when the spring-loaded coupler cover 152 is in the closed position.

Figure 4:
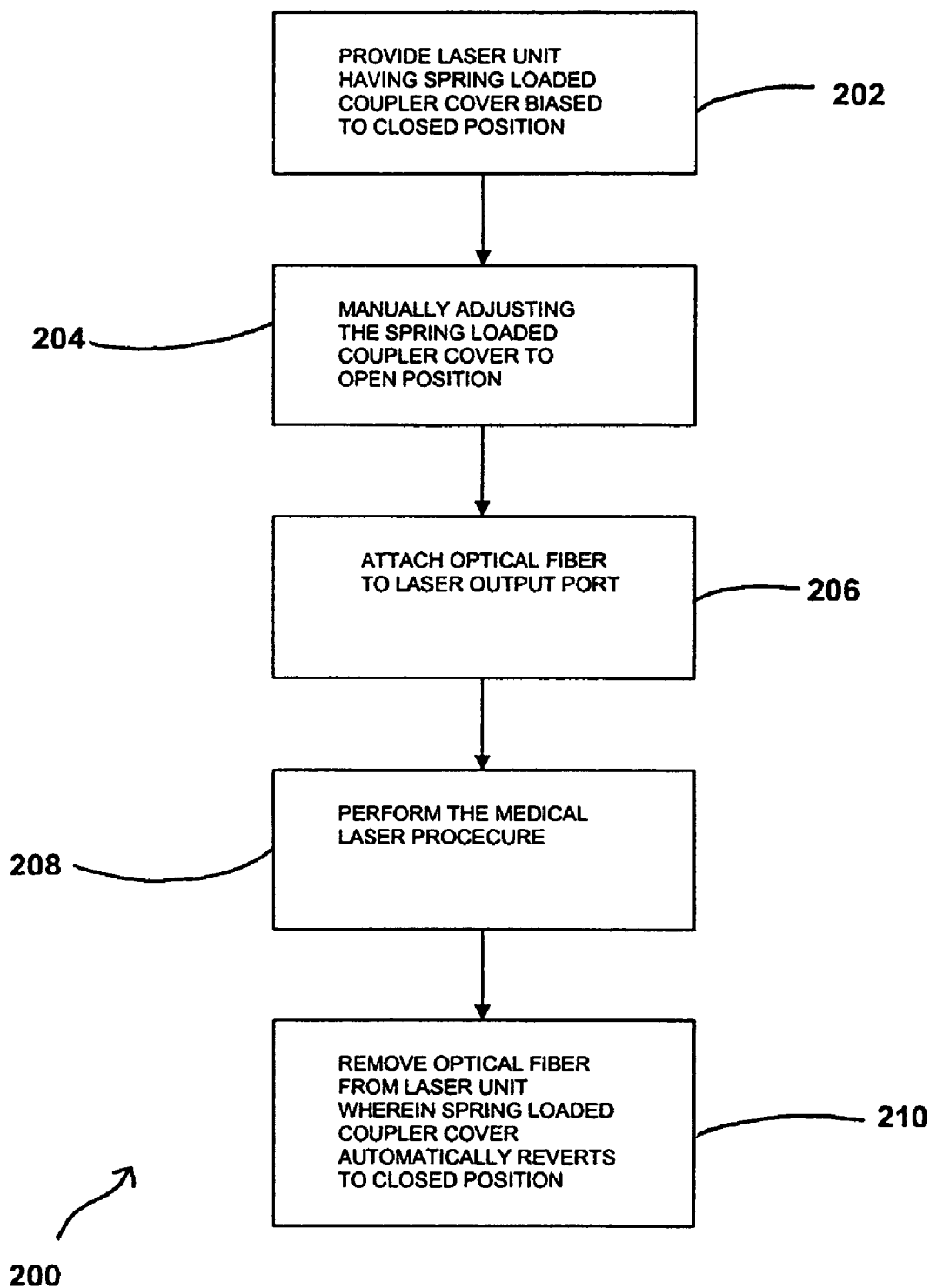
FIG. 4 depicts a flow chart describing a method of protecting a laser unit from dust infiltration when an optical fiber is detached from the laser unit according to an embodiment of the present invention.

A representative method 200 of protecting the fiber optic coupler 150, particularly when no optical fiber 106 is attached to the laser unit 102 is illustrated schematically in FIG. 4. The method generally includes a first step 202 of providing a laser unit having a spring-loaded coupler cover 152 biased to a closed position 164 proximate a fiber optic coupler 150. A second step 204 involves manually adjusting the spring-loaded coupler cover 152 to an open position 166 wherein an output port 118 is exposed within the fiber optic coupler 150. A third step 206 includes attaching an optical fiber 106 to the laser unit by coupling the optical fiber 106 to the output port 118. With the optical fiber 106 attached to the laser unit 106, the spring-loaded coupler cover 152 resides against the fiber connector 166. A fourth step 208 involves performing the medical laser procedure utilizing the laser unit 102 to deliver laser energy to tissue 104 through the tip 140. A fifth step 210 involves removing the optical fiber 106 from the output port 118, wherein the spring-loaded coupler cover 102 is automatically biased to closed position 164 over the fiber optic coupler 150 to prevent infiltration of dust into the aperture 153 and output port 118. As the spring-loaded coupler cover 152 closes automatically in the absence of a connected optical fiber 106, there is no need to find and place a cover on fiber optic coupler 150 as is necessary with prior art laser devices.

Although specific examples have been illustrated and described herein, it will be appreciated by those of ordinary skill in the art that any arrangement calculated to achieve the same purpose could be substituted for the specific examples shown. This application is intended to cover adaptations or variations of the present subject matter. Therefore, it is intended that the invention be defined by the attached claims and their legal equivalents.

The invention claimed is:

1. A medical laser unit comprising:
   a laser unit having a fiber optic coupler,
   an optical fiber; and
   a spring-biased coupler cover mounted to the laser unit proximate the fiber optic coupler, the spring loaded coupler cover including a biasing spring such that the spring loaded coupler cover is automatically biased to a closed position covering the fiber optic coupler and is manually positionable to an open position when attaching the optical fiber to the fiber optic coupler, the spring biased coupler including a biasing spring and a low-friction cam follower mounted over the biasing spring, the low-friction cam follower in direct communication with the spring-based coupler cover.

2. The medical laser of claim 1, wherein the spring-biased coupler cover is attached to the laser unit with a hinge assembly such that the spring-biased coupler cover is rotatably moveable between the closed position and the open position.

3. The medical laser of claim 2, further including a cam profile proximate the hinge assembly, wherein the cam profile is in direct communication with the spring loaded coupler cover.

4. The medical laser unit of claim 3, wherein the cam follower and the cam profile interact to minimize biasing force applied by the spring loaded coupler cover to a fiber connector on the optical fiber when the optical fiber is connected to the fiber optic coupler.

5. The medical laser unit of claim 1, wherein the spring loaded coupler cover includes a positioning structure adapted for insertion into an aperture on the fiber optic coupler such that the spring loaded coupler cover is aligned over the aperture when the spring loaded coupler cover is biased to the closed position.

6. The medical laser unit of claim 1, wherein the spring loaded coupler cover further comprises a dust seal positioned to seal against the fiber optic coupler with the spring loaded coupler cover in the closed position.

7. A method for maintaining performance of a medical laser comprising:
- providing a laser unit including a fiber optic coupler;
- attaching a spring-loaded cover directly to the laser unit proximate the fiber optic coupler, the spring-loaded coupler cover biased to a closed position a covering the fiber optic coupler;
- shifting the spring loaded coupler cover to an open position to expose the fiber optic coupler;
- attaching an optical fiber to the laser unit by coupling the optical fiber to the fiber optic coupler; and
- reducing force applied by the spring loaded coupler cover to the attached optical fiber by providing a spring-biased cam follower in contact with a cam profile on the spring loaded coupler cover.

8. The method of claim 7, wherein shifting the spring loaded coupler cover to an open position further comprises rotatably shifting the spring loaded coupler cover to the open position about a hinge assembly attaching the spring loaded coupler cover to the laser unit.

9. The method of claim 7, further comprising:
- biasing the spring loaded coupler cover toward a closed position whenever the spring loaded coupler cover is shifted to the open position.

10. The method of claim 9, further comprising:
- removing the optical fiber from the fiber optic coupler upon completion of a medical laser procedure, wherein the spring loaded coupler cover is automatically directed to the closed position over the fiber optic coupler.

11. The method of claim 10, further comprising:
- guiding the spring loaded coupler cover into the closed position with a positioning structure adapted for insertion into an aperture on the fiber optic coupler.

12. The method of claim 10, further comprising:
- eliminating any air gap between the spring loaded coupler cover and the fiber optic coupler when the spring loaded coupler cover is in the closed position by attaching a dust seal to the spring loaded coupler cover such that the dust seal prevents exposure of the laser output port to dust when the spring loaded coupler cover is in the closed position.

13. A medical laser unit comprising:
- a laser unit having a fiber optic coupler proximate an output port,
- an optical fiber; and
- a spring-biased coupler cover mounted to the laser unit, the spring-biased coupler cover attached to the laser unit with a hinge assembly such that the spring-biased coupler cover is rotatably moveable between a closed position and an open position, the spring-biased coupler including a biasing spring and a low-friction cam follower mounted over the biasing spring, the low-friction cam follower in direct communication with the spring-biased coupler cover such that the spring loaded coupler cover is automatically biased to the closed position covering the fiber optic coupler and is manually positionable to the open position when attaching the optical fiber to the fiber optic coupler.

14. method for maintaining performance of a medical laser comprising:
- providing a laser unit having a spring-loaded coupler cover biased to a closed position proximate a fiber optic coupler;
- shifting the spring loaded coupler cover to an open position to expose a laser output port on the fiber optic coupler;
- attaching an optical fiber to the laser unit by coupling the optical fiber to the laser output port
- biasing the spring loaded coupler cover toward the closed position when the optical fiber is coupled to the laser output port; and
- reducing force applied by the spring loaded coupler cover to the attached optical fiber by providing a spring-biased cam follower in contact with a cam profile on the spring loaded coupler cover.

* * * * *